United States Patent
Maeding et al.

(10) Patent No.: US 7,482,498 B2
(45) Date of Patent: Jan. 27, 2009

(54) DEVICE AND PROCESS FOR NUCLEOPHILIC FLUORINATION

(75) Inventors: Peter Maeding, Dresden (DE); Frank Fuechtner, Dresden (DE)

(73) Assignee: Schering AG, Berlin (DE)

( * ) Notice: Subject to any disclaimer, the term of this patent is extended or adjusted under 35 U.S.C. 154(b) by 540 days.

(21) Appl. No.: 10/840,429

(22) Filed: May 7, 2004

(65) Prior Publication Data

US 2009/0005617 A1 Jan. 1, 2009

Related U.S. Application Data

(60) Provisional application No. 60/468,963, filed on May 9, 2003.

(30) Foreign Application Priority Data

May 7, 2003 (DE) .............................. 103 20 522

(51) Int. Cl.
- C07C 17/00 (2006.01)
- G10K 11/00 (2006.01)
- G01L 25/00 (2006.01)
- B01L 3/00 (2006.01)

(52) U.S. Cl. .................... 570/101; 702/23; 73/1.67; 422/99

(58) Field of Classification Search ............ 570/101
See application file for complete search history.

(56) References Cited

U.S. PATENT DOCUMENTS 5,932,178 A 8/1999 Yamazaki et al.

FOREIGN PATENT DOCUMENTS

EP 0949632 10/1999

OTHER PUBLICATIONS

Jalilian, Amir Reza et al. "A new method for one-step no carrier added synthesis of cholesteryl 4 18F-fluorobenzoate" Jour Pharmacy and Pharmaceutical Sciences. 2000. 3(1) 118-124.*
Zhang et al. Development of an automated system for synthesizing 18F-labeled compounds using [18F]fluoroethyl bromide as a synthetic precursor. Applied Radiation and Isotopes 57 (2002) 335-342.*
S. A. Toorongian et al., "Routine production of 2-deoxy-2[18F]fluoro-D-glucose by direct nucleophillic exchange on a quaternary 4-aminopyridinium resin," Nucl. Med. Biol., 1990, pp. 273-279, vol. 17, No. 3, XP000676335.

* cited by examiner

*Primary Examiner*—Daniel M Sullivan
*Assistant Examiner*—Lousia Lao
(74) *Attorney, Agent, or Firm*—Millen, White, Zelano, & Branigan, P.C.

(57) ABSTRACT

The invention relates to a device and a process for nucleophilic fluorination of a substance, especially for synthesis of an $^{18}F$-labeled substance for examination using a positron emission tomograph. The device comprises an anion exchange device (102) for extraction of [$^{18}F$]fluoride ions by means of adsorption from a target fluid, whereby the anion exchange device (102) can be charged via a supply device (101) with the target fluid; and a measurement device (104) with a measurement chamber (103) for measuring initial radioactivity of the [$^{18}F$]fluoride ions, the anion exchange device (102) being arranged at least partially in the measurement chamber (103) of the measurement device (104).

16 Claims, 3 Drawing Sheets

DEVICE AND PROCESS FOR NUCLEOPHILIC FLUORINATION

This application claims the benefit of the filing date of U.S. Provisional Application Ser. No. 60/468,963 filed May 9, 2003.

FIELD OF THE INVENTION

The invention relates to the area of nucleophilic fluorination of a substance, especially for synthesis of an $^{18}$F-labeled substance for examination using a positron emission tomograph.

BACKGROUND OF THE INVENTION

Positron emission tomography (PET) is a technology of nuclear medicine in which radiopharmaceutical agents are used that are formed from biologically relevant molecules that are labeled with positron-emitting isotopes. PET is used to study metabolic processes and physiological processes. Based on the use of analysis of radiation of short-lived radioisotopes of elements that are found in the human body, PET delivers additional information to other diagnostic processes, such as, for example computer-based tomography or examinations using magnetic resonance. PET radiopharmaceutical agents participate in biochemical reactions of the body with a dose that is not critical for humans.

The utility of PET depends essentially on the availability of nontoxic radiopharmaceutical agents. Fluorine-18 ($^{18}$F) has proven to be one of the preferred radioisotopes because its decay energy of 0.64 MeV makes possible a high inherent resolution during PET measurements. $^{18}$F, moreover, has an advantageous half-life of 109.8 minutes. In the past, especially 2-[$^{18}$F]fluoro-2-desoxy-D-glucose ([$^{18}$F]FDG) has been successfully used. This labeling substance is used worldwide for the most varied applications. [$^{18}$F]FDG is a sugar compound that is labeled with $^{18}$F and that can be easily administered to a patient. [$^{18}$F]FDG is easily processed by growing cancer cells, the brain or cardiac muscles. The described properties of [$^{18}$F]FDG have led to its being successfully used in nuclear medicine. The use of PET in clinical applications has led to development of devices for synthesizing radiopharmaceutical agents such as [$^{18}$F]FDG.

The publication by N. Satyamurthy: Electronic Generators for the Production of Positron-Emitter-labeled Radiopharmaceutical Agents: Where Would PET Be Without Them? Clinical Positron Imaging, Vol. 2, No. 5, pages 233-253, 1999, describes in survey form various devices for automated FDG synthesis.

Document U.S. Pat. No. 5,932,178 discloses an FDG synthesis module with a column that is filled with a polymer-supported catalysis resin. Document U.S. Pat. No. 5,808,020 describes an optical reaction cell and a light source for processes for synthesis of $^{18}$F-labeled radiotracers using [$^{18}$F]fluoride.

Document WO 02/36581 describes novel radiopharmaceutical agents that bind to the CCR1 receptor, which occurs in conjunction with Alzheimer's disease in the brain areas of patients.

Based on the search for novel, suitable radiopharmaceutical agents that are based on new synthesis processes, there is a demand for devices that can be used for the synthesis of radiopharmaceutical agents.

The Invention

The object of the invention is therefore to devise an improved device and an improved process for nucleophilic fluorination that makes possible application-dependent synthesis of nucleophilically fluorinated substances in a manner that is suitable for flexible clinical applications.

This object is achieved according to the invention by a device according to independent claim 1 and a process according to independent claim 9.

A device that is used for nucleophilic fluorination of a substance, especially for synthesis of an $^{18}$F-labeled substance for examination using a positron emission tomograph, comprises an anion exchange device for extraction of [$^{18}$F]fluoride ions by means of adsorption from a target fluid, and the anion exchange device can be charged via a supply device with the target fluid, and a measurement device with a measurement chamber for measuring the initial radioactivity of the [$^{18}$F]fluoride ions. Here, the anion exchange device is located at least partially in the measurement chamber of the measurement device. This has the advantage that the initial radioactivity of the [$^{18}$F]fluoride ions can be measured while they are in the anion exchange device. Because of an additional collecting vessel for the target fluid, no losses occur.

In one feasible further development of the invention, there is a vessel for holding a nucleophilically fluorinated reaction product, the vessel being located at least partially in the measurement chamber of the measurement device in order to measure the radioactivity of the nucleophilically fluorinated reaction product. In this way, the initial radioactivity and the radioactivity of the reaction product can be measured using an individual measurement device. Both measurements can be taken without the need to move or re-arrange parts of the measurement device.

The accuracy of the radioactivity measurements is improved in one feasible configuration of the invention in that the measurement device is a measurement device that can be calibrated. This has the advantage, moreover, that in a subsequent measurement, background radioactivity due to residues in the measurement chamber can be eliminated by compensation of the background radioactivity as measured value adulteration.

A compactly executable measurement device that is provided with the required accuracy can be formed in one advantageous further development of the invention in that the measurement device is an activity meter. An activity meter is used for fast and accurate determination of the radioactivity of radionuclides. Important advantages of radioactivity measurement with an activity meter consist in 4-π measurement geometry, the large linear measurement range and the nuclide-specific calibration.

The use of the device for nucleophilic fluorination, in which purity of the reaction product that is as great as possible is necessary, is made possible in one advantageous embodiment of the invention in that there is an HPLC device (HPLC—"High Performance Liquid Chromatography") with an HPLC column for purifying a reaction mixture. Such an HPLC device that is also called preparative HPLC is used for isolation and purification of components. In nucleophilic reactions, reaction mixtures often occur that can be separated using the HPLC device.

One preferred development of the invention can provide that the HPLC device comprises a sample feed valve that is connected to a coupling line for charging the metering device; the sample feed valve is coupled via a waste line to a waste tank; a fluid sensor device is connected upstream from the sample feed valve for detecting the reaction mixture in the coupling line; and the sample feed valve is made to be controllable so that the sample feed valve is set in the initial state in order to form, via the metering device, a fluid connection between the coupling line and the waste line, when using the fluid sensor device the reaction mixture in the supply line is detected, and the sample feed valve is switched into an injection state for charging the HPLC column in order to form a fluid connection between the metering device and the HPLC column in the injection state, when the reaction mixture is no longer being detected in the supply line using the fluid sensor device. Using this configuration prevents the fact that when the HPLC device is being charged with the reaction mixture, air that is in the lines connected upstream from the HPLC device is transferred into the metering device of the HPLC device before the reaction mixture travels into these lines; this could adversely affect the yield of the isolation and the effectiveness of separation in the HPLC device.

One feasible configuration of the invention can provide for formation of a direct coupling between the fluid sensor device and a reaction vessel by means of the coupling line. Direct coupling reduces the probability of losses in the transfer of the reaction mixture.

One feasible embodiment of the invention can provide for the HPLC device to comprise a purification device with a UV detector device and a gamma detector device that follows the UV detector device for purifying the reaction mixture using the UV detector device and then using the gamma detector device. This arrangement makes it possible to isolate a radioactive peak such that as few chemical impurities as possible with the corresponding UV absorption are contained, and the losses of the radioactive end product can be minimized.

The features from the dependent claims of the process for nucleophilic fluorination of a substance have the advantages named in conjunction with the pertinent features in the dependent device claims.

BRIEF DESCRIPTION OF THE FIGURES

The invention is explained in more detail below using embodiments with reference to a drawing.

Here.

DETAILED DESCRIPTION OF PREFERRED EMBODIMENTS

Figure 1:
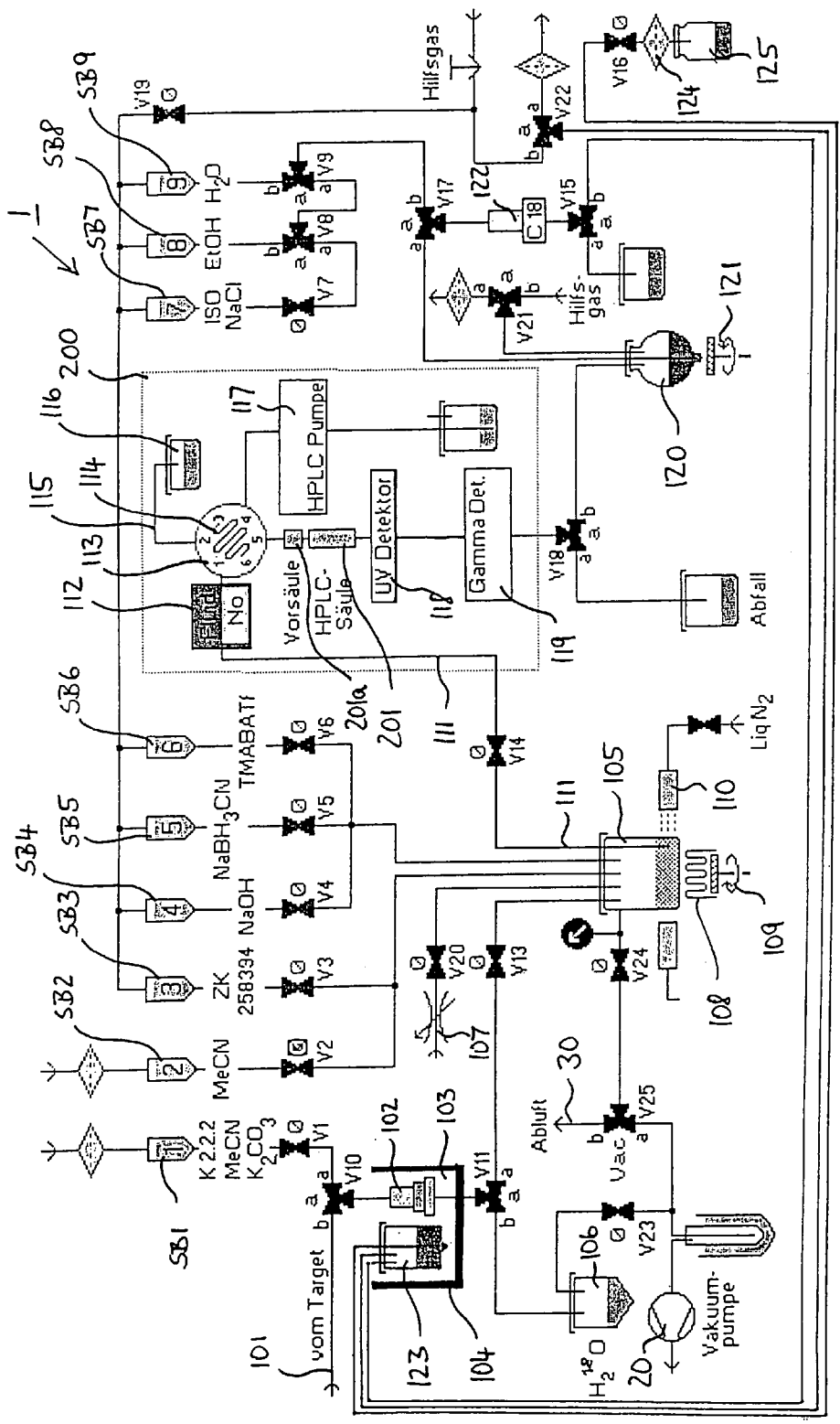
FIG. 1 shows a diagrammatic visualization of a device for nucleophilic fluorination of a substance.
Figure 2:
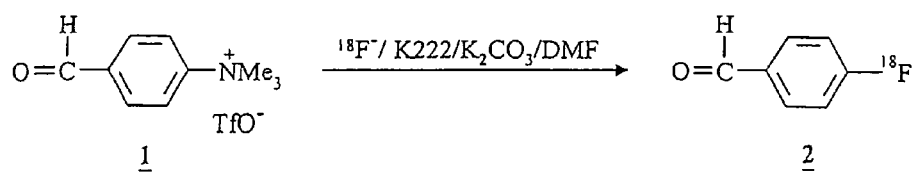
FIG. 2 shows a synthesis diagram for 4-[$^{18}$F]FBA (2) from TMABATf(1) and [$^{18}$F]fluoride.
Figure 3:
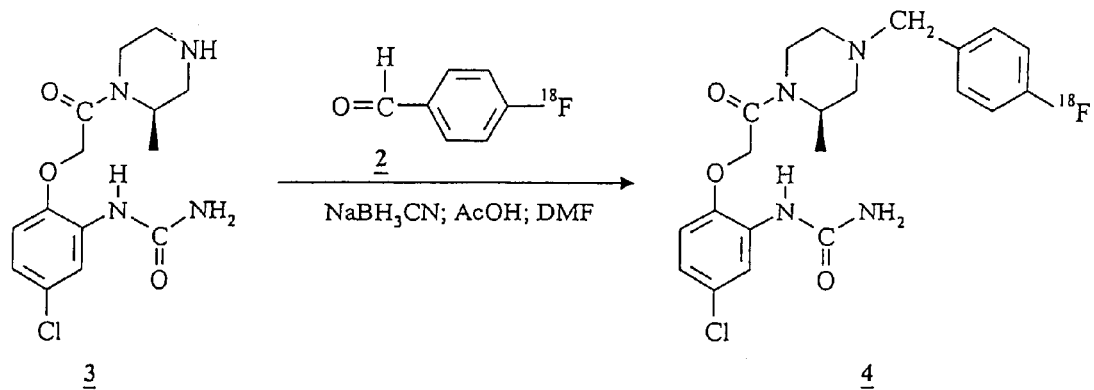
FIG. 3 shows a synthesis diagram for [18f]ZK8111460 (4) from a piperazine derivative (3) and [18F]FBA (2)

FIG. 1 shows a diagrammatic representation of a device 1 for nucleophilic fluorination of a substance. The use of the device 1 for synthesis is explained using the example of the production of the labeled compound 1-(5-chloro-2-{2-[(2R)-4-(4-[$^{18}$F]fluorobenzyl)-2-methylpiperazine-1-yl]-2-oxoethoxy}phenyl)urea, which is formed starting from TMA-BATf (1) by means of radiosynthesis of 4-[$^{18}$F]FBA (2) and its reductive amination with a piperazine derivative (3) (cf. FIGS. 2 and 3). The labeled compound that is obtained in this way is hereinafter abbreviated [$^{18}$F]ZK811460 (4). Other specific details, especially with respect to the chemical substances used and reaction parameters, if they do not follow from the following description, can be taken from the publication by Mading, et al., Annual Report 2002, Institute of Bioorganic and Radiophar-maceutical Chemistry, FRZ-363, 40, and are not critical for the implementation of the invention in its different embodiments.

The [$^{18}$F]fluoride ions contained in a target fluid are supplied via a supply 101 and a valve V10 to an anion exchange device 102. The anion exchange device 102 is used to extract [$^{18}$F]fluoride ions from the target fluid. The extraction is done using adsorption. According to FIG. 1, the anion exchange device 102 is located in a measurement chamber 103 of a measurement device 104 that is used for measuring the radioactivity. In this connection, the measurement device 104 is made preferably as an activity meter. Using the measurement device 104, the initial radioactivity of [$^{18}$F]fluoride ions can be measured during and after their extraction from the target fluid using the anion exchange device 102.

The anion exchange device 102 is connected via a valve V10 to the supply 101 and a valve V1. Via the valve V1, substances that are available in the storage tank SB1 can be delivered to the valve V10. In this connection, the substances are transferred using a vacuum or in an alternative manner by means of a gas, for example nitrogen, through lines and valves. The anion exchange device 102 is furthermore coupled to a valve V11 via which the extracted [$^{18}$F]fluoride ions after their desorption after passing through a valve V13 travel into a reaction vessel 105. Via the valve V11, [$^{18}$O]H$_2$O that is separated by opening the valve V23 with the vacuum pump 20 that is turned on travels from the anion exchange device 102 into a tank 106. The valves V24 and V25 are used to apply a vacuum to the reaction vessel 105 or to ventilate it.

According to FIG. 1, the reaction vessel 105 is connected to other valves V2, V3, V4, V5 and V6 that are coupled to the respective storage tank SB2-SB6. Via the valves V2-V6, the chemical substances stored in the respective storage tanks SB2-SB6 can be added in a given volume to the reaction vessel 105 in order to carry out the desired chemical reaction for synthesis of [$^{18}$F]ZK811460 (4). In this connection, the substances are transferred using a vacuum or in an alternative manner by means of a gas, for example nitrogen, through lines and valves. A valve V20 is used to control the feed of protective gas from a line 107 to the reaction vessel 105. To remove the exhaust gases that form in the chemical reaction, the reaction vessel 105 is furthermore connected via a valve V24 and V25 to an exhaust gas opening 30.

To synthesize [$^{18}$F]ZK811460 in the reaction vessel 105, first the [$^{18}$F]fluoride is eluted with a solution of Kryptofix 2.2.2 and potassium carbonate in aqueous acetonitrile (from SB1) from the anion exchange device 102 and is dried by means of a vacuum and nitrogen stream at 95° C. Additional drying takes place by adding anhydrous acetonitrile (from SB2) and its vaporization. After adding a solution of TMA-BATf (1) in DMF (from SB6), the reaction mixture 10 is heated for 10 minutes at 120° C. Then, in succession, an acetic acid solution of the piperazine precursor (3) (ZK258394 from SB3) and a solution of NaBH$_3$CN in DMF (from SB5) are added. After 10 minutes of heating at 120° C., the reaction mixture is neutralized with aqueous NaOH (from SB4).

To adjust the desired reaction parameters, in the area of the reaction vessel 105, there are a heating device 108, a stirring device 109 and a cooling device 110.

Via a direct coupling line 111 in which there is a valve V14, the reaction mixture [$^{18}$F]ZK811460 (4) travels to a fluid sensor 112 that detects a fluid in the direct coupling line 111. The fluid sensor 112 is connected directly upstream from an injection valve or sample feed valve 113, the operation of which is described below with reference to FIGS. 1 and 4, the latter showing a diagrammatic representation of a 6-way sample feed valve. Using the sample feed valve 113, a metering loop 114 is charged via a direct coupling line 111 to the reaction mixture. Here, the sample feed valve 113 is controlled such that first via points 1 and 2 (cf. FIG. 4), a connection is formed between the direct coupling line 111 and the fluid sensor 112 and a waste line 115 that leads from the sample feed valve 113 to a waste tank 116. In this way, air that is located in the direct coupling line 111 in front of the reaction mixture is forced into the waste line 115. In this position of the sample feed valve 113 (injection state), the metering loop 114 is flushed by an HPLC eluent, the HPLC eluent in the sample feed valve 113 traversing a path along points 4, 3, 6 and 5.

Figure 4:
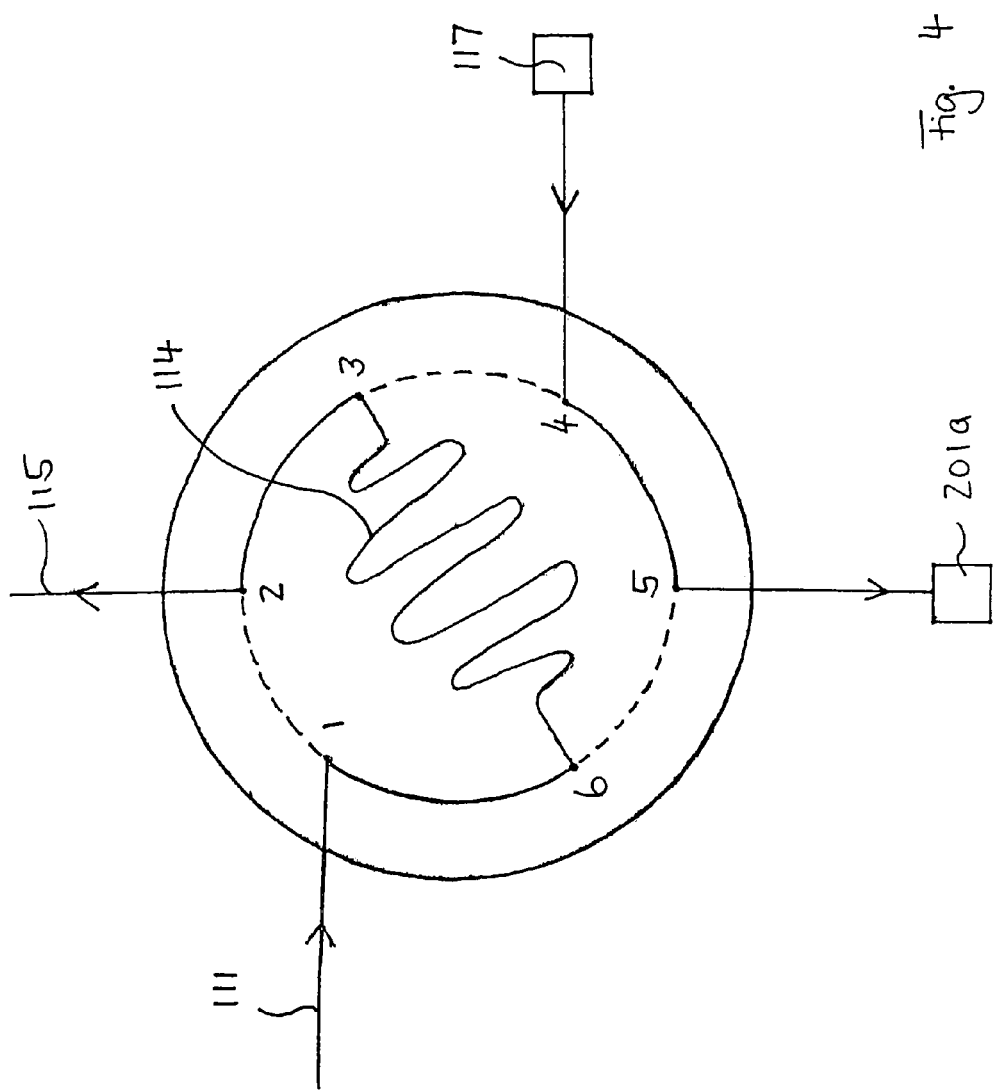
FIG. 4 shows a diagrammatic visualization of a sample feed valve.

When the fluid sensor 112 detects the arrival of the reaction mixture from the reaction vessel 105, the sample feed valve 113 for charging the metering loop 114 is switched into the charging state so that via the metering loop 114, a connection between the direct coupling line 111 and the waste line 115 along the points 1, 6, 3, and 2 is formed, which is shown in FIG. 4 by the continuous lines, and leads to the metering loop's 114 being charged with the reaction mixture. The volume of the metering loop 114 is generally greater than the volume of the reaction mixture. The HPLC eluent passes through the sample feed valve 113 via a short circuit along a path with points 4 and 5 in FIG. 4. If the reaction mixture is no longer being detected by the fluid sensor 112, the sample feed valve 113 is switched again into the injection state so that a connection is formed along the path with the points 4, 3, 6, and 5 (broken line in FIG. 4). The HPLC eluent can then force the reaction mixture out of the metering loop 114 to an HPLC column 201 with a precolumn 201a.

Using the HPLC device 200, the reaction mixture is purified. Depending on the specific use of the device 1 for different synthesis purposes, the parameters on the HPLC device 200 can be set and optimized according to the desired purpose.

The HPLC device 200 in this embodiment shown comprises an HPLC pump 117, the sample feed valve 113 with the metering loop 114, the HPLC column 201 with precolumn 201a as well as a UV detector device 118 and a gamma detector device 119, which are arranged in series.

Via a valve V18, a mixing tank 120 with a water receiver and a stirring device 121 and a valve V17, the isolated product fraction travels to an RP18 cartridge 122 for collecting the reaction product by means of solid-phase extraction. After washing the cartridge 122 with water (from SB9), [$^{18}$F] ZK811460 (4) is eluted by means of ethanol (from SB8). The ethanolic solution of [$^{18}$F]ZK811460 (4) is then routed for filtering out of the elution vessel 123 through a sterilizing filter 124 that afterwards is flushed with an injection solution based on salt (from SB7). In this way, a clear, sterile isotonic NaCl solution of [$^{18}$F]ZK811460 (4) is obtained that contains ethanol and is collected in a product vessel 125. The elution vessel 123 is arranged in the measurement chamber 103, which makes possible direct measurement of the radioactivity of the reaction product [$^{18}$F]ZK811460 (4). In one preferred embodiment of the measurement device 104 that can be calibrated, when the radioactivity of the reaction product is measured, the radioactivity background can be compensated such that residual radioactivity that is still present after dissolving out the [$^{18}$F]fluoride ions in the anion exchange device 102 is compensated as the background radioactivity of the radioactivity measurement of the reaction product that is to be carried out. The measurement of the initial radioactivity in the anion exchange device 102 and the radioactivity of the reaction product in the elution vessel 123 can be carried out in this way with high precision using the measurement device 104.

The features of the invention that are disclosed in the description above, the claims and the drawings can be important both individually and also in any combination for the implementation of the invention in its different embodiments.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 103 20 552.7, filed May 7, 2003, and U.S. Provisional Application Ser. No. 60/468,963, filed May 9, 2003 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A device for nucleophilic fluorination of a substance with an $^{18}$F isotope, which comprises:
    an anion exchange device for extraction of $^{18}$F-fluoride ions by means of adsorption from a target fluid, including a supply device for charging the anion exchange device with the target fluid, and
    a measurement device with a measurement chamber for measuring the initial radioactivity of the extracted $^{18}$F-fluoride ions;
the anion exchange device being located at least partially in the measurement chamber of the measurement device such that measurement of the initial radioactivity of the $^{18}$F-fluoride ions can be conducted while they are in the anion exchange device, and
    an HPLC device comprising a sample feed valve.

2. A device according to claim 1, further comprising means for contacting the extracted $^{18}$F-fluoride ions with the substance in order to nucleophilically fluorinate the substance with an $^{18}$F isotope.

3. A device according to claim 2, further comprising a vessel for holding the substance which has been nucleophilically fluorinated with an $^{18}$F isotope, the vessel being arranged at least partially in the measurement chamber of the measurement device such that measurement of the radioactivity of the substance in the vessel can be conducted.

4. A device according to claim 1, wherein the measurement device is a measurement device that can be calibrated.

5. A device according to claim 1, wherein the measurement device is an activity meter.

6. A device according to claim 2, further comprising an HPLC device with an HPLC column for purifying the substance which has been nucleophilically fluorinated with an $^{18}$F isotope.

7. Device according to claim 6, wherein the HPLC device comprises
    a sample feed valve that is connected to a coupling line for charging a metering device wherein the sample feed valve is coupled via a waste line to a waste tank; and a fluid sensor device connected upstream from the sample feed valve for detecting the reaction mixture in the coupling line;

wherein:

the sample feed valve is controllable such that the sample feed valve is set into an initial state to form, via the metering device, a fluid connection between the coupling line and the waste line when the reaction mixture in the supply line is detected using the fluid sensor device, and the sample feed valve being switched into an injection state for charging the IIPLC column to form a fluid connection between the metering device and the HPLC column in the injection state, when the reaction mixture is no longer detected in the supply line by the fluid sensor device.

8. A device according to claim 7, wherein a direct coupling is formed between the fluid sensor device and a vessel containing a substance which has been nucleophilically fluorinated with an $^{18}$F isotope by means of the coupling line.

9. A device according to claim 6, wherein the HPLC device comprises a purification device having a UV detector device followed by a gamma detector device in series for purifying a substance which has been nucleophilically fluorinated with an $^{18}$F isotope.

10. A process for nucleophilic fluorination of a substance with an $^{18}$F isotope, which comprises:

in an anion exchange device, extracting $^{18}$F-fluoride ions by adsorption from a target fluid, whereby the anion exchange device is charged via a supply device with the target fluid;

measuring the initial radioactivity of the $^{18}$F-fluoride ions using a measurement device with a measurement chamber, wherein the anion exchange device is located at least partially in the measurement chamber of the measurement device to allow such measuring; and contacting the extracted $^{18}$F-fluoride ions with a substance in order to nucleophilically fluorinate the substance with an $^{18}$F isotope.

11. A process according to claim 10, wherein the radioactivity of the substance nucleophilically fluorinated with an $^{18}$F isotope is measured in a vessel for holding the substance which is located at least partially in the measurement chamber of the measurement device.

12. A process according to claim 10, wherein the measurement device for measuring the radioactivity of the substance nucleophilically fluorinated with an $^{18}$F isotope is calibrated.

13. A process according to claim 10, wherein the measurement device is an activity meter.

14. A process according to claim 10, wherein the substance nucleophilically fluorinated with an $^{18}$F isotope is purified using an HPLC device that comprises an HPLC column.

15. A process according to claim 14, in which:

the HPLC column is charged via a coupling line and a metering device;

a sample feed valve of the HPLC device is connected via a waste line to a waste tank;

a fluid sensor device is connected upstream from the sample feed valve for detecting the reaction mixture in the coupling line; and the sample feed valve is controlled such that:

the sample feed valve is set in the initial state to form via a metering device a fluid connection between the coupling line and the waste line in the initial state, when the reaction mixture in the supply line is detected using the fluid sensor device, and the sample feed valve is switched into an injection state for charging the HPLC column to form a fluid connection between the metering device and the HPLC column in the injection state, when the reaction vessel is no longer being detected in the supply line using the fluid sensor device.

16. A process according to claim 14, wherein the purified the substance nucleophilically fluorinated with an $^{18}$F isotope is routed as an ethanolic solution through a filter device and wherein the filter device is flushed afterwards with an injection solution in order to form an injectable, sterile reaction product solution.

* * * * *